United States Patent [19]

Shamp

[11] Patent Number: 4,872,879
[45] Date of Patent: Oct. 10, 1989

[54] PROSTHETIC DEVICE FOR ABOVE-KNEE AMPUTATION

[75] Inventor: Daniel L. Shamp, Akron, Ohio

[73] Assignee: Prosthetic Consultants Inc., Akron, Ohio

[21] Appl. No.: 99,778

[22] Filed: Sep. 22, 1987

[51] Int. Cl.$^4$ ............................................. A61F 2/80
[52] U.S. Cl. ...................................................... 623/36
[58] Field of Search .................................. 623/33–38, 623/61–65

[56] References Cited

U.S. PATENT DOCUMENTS

| Re. 11,522 | 1/1896  | Hershberger | 623/36 |
|------------|---------|-------------|--------|
| 129,340    | 7/1872  | Hawkins     | 623/33 |
| 912,130    | 2/1909  | James       | 623/35 |
| 977,974    | 12/1910 | Showalter   | 623/35 |
| 1,216,367  | 2/1917  | Rowley      | 623/33 |
| 2,273,695  | 2/1942  | Dew         | 623/33 |
| 3,111,683  | 11/1963 | Bach        | 623/38 |
| 4,128,903  | 12/1978 | Marsh       | 623/36 |

FOREIGN PATENT DOCUMENTS

| 1044325 | 11/1953 | France         | 623/34 |
| 2069847 | 9/1981  | United Kingdom | 623/35 |
| 2103490 | 2/1983  | United Kingdom | 623/33 |

*Primary Examiner*—Richard J. Apley
*Assistant Examiner*—James Prizant
*Attorney, Agent, or Firm*—Renner, Kenner, Greive, Bobak, Taylor & Weber

[57] ABSTRACT

An ischial containment socket (10) having a frame (12) that is separate from, and is capable of being selectively secured to, an interface (11). The interface (11) has proximal and distal ends (14 and 15) and at least the proximal end (14) is open to receive the residual limb of an above-knee amputation. The interface (11) has four walls (16, 18, 19 and 20), and the dimension between the medial and lateral walls (18 and 19) is less than the dimension between the posterior and the anterior walls (16 and 20). The proximal ends of the adjacent posterior and medial walls (16 and 18) present a containment brim (30). The brim (30) is in the form of a flared offset wall (31) that extends generally outwardly and upwardly from the proximal ends of the adjacent posterior and medial walls (16 and 18). A reversely curved containment recess (32) is provided in the flared offset wall (31). The interface (11) has a peripheral discontinuity (26) along the longitudinal extent thereof which permits adjusting the peripheral dimension of the interface to facilitate fitting of the interface (11) to a residual limb. A cinch means (28) is employed to secure the desired peripheral dimension of the interface (11) properly to circumscribe the residual limb received therein. The frame (12) is located at the distal end (15) of the interface (11), and means (43 and 44) are provided selectively to secure the frame (12) to the interface (11) in the desired, relative position.

9 Claims, 3 Drawing Sheets

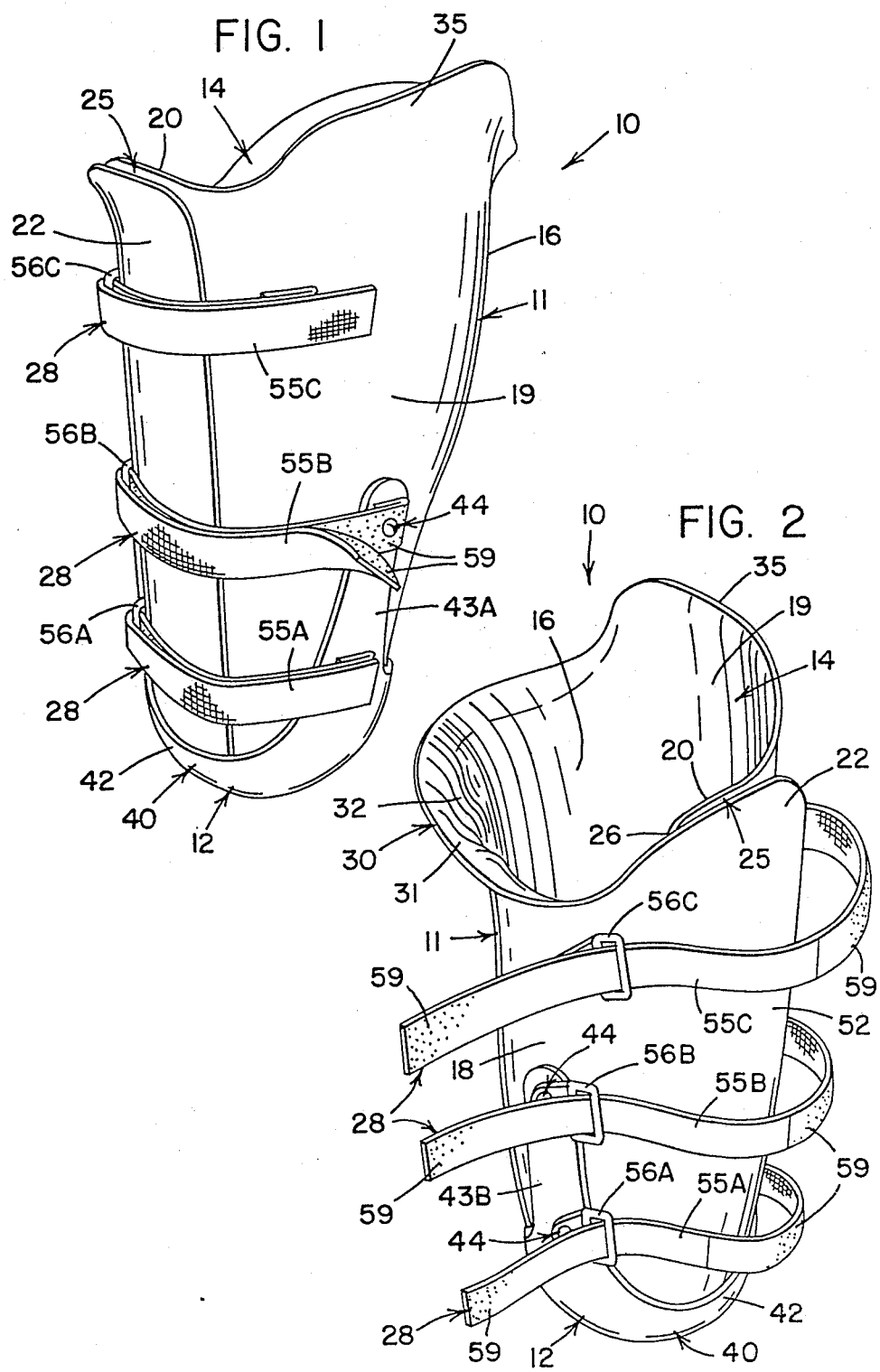

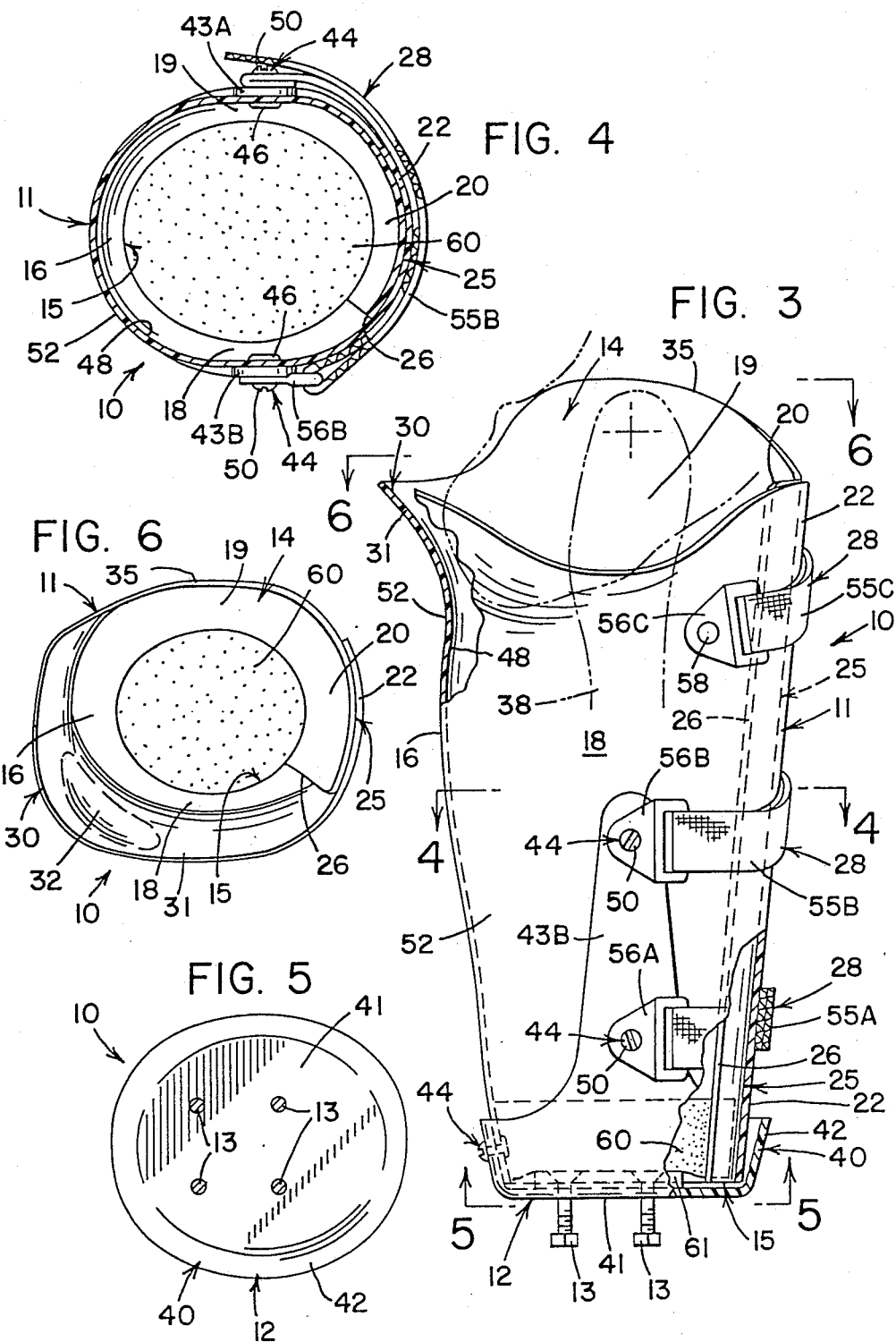

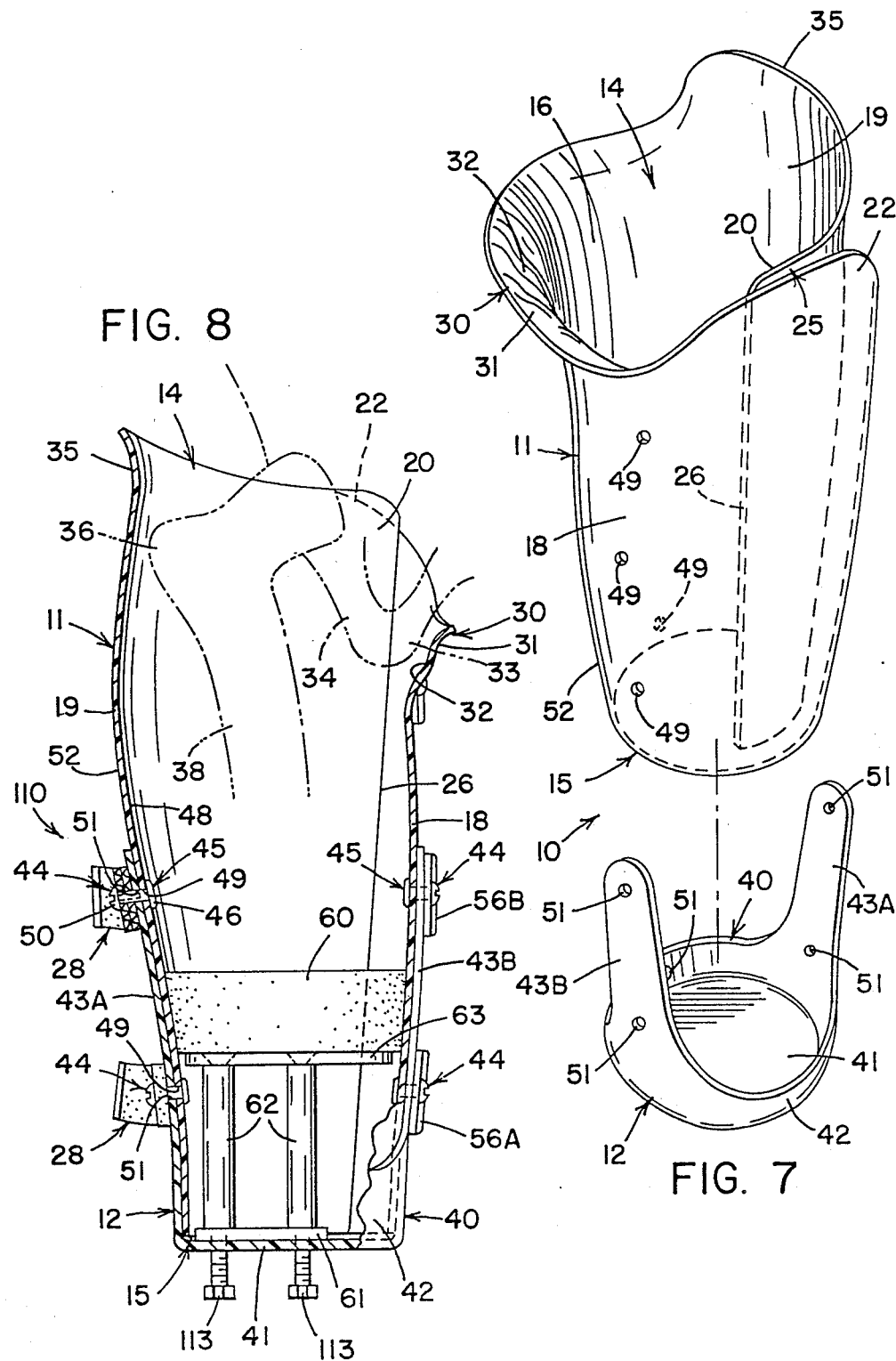

PROSTHETIC DEVICE FOR ABOVE-KNEE AMPUTATION

TECHNICAL FIELD

The present invention relates to a prosthetic socket arrangement for securing an artificial limb to the residual thigh of an above-knee amputee. More particularly, the present invention relates to a prosthetic socket that incorporates the recently developed, relatively narrow, medial/lateral dimension in comparison to the anterior/posterior dimension. Specifically, the present invention relates to the provision of a standardized prosthetic socket arrangement which incorporates the narrow, medial/lateral dimension; which can be provided in a minimal number of sizes; and, which can be conveniently adapted, and adjustably fitted, to the residual limbs of the vast majority of above-knee amputees without extensive custom fitting.

BACKGROUND OF THE INVENTION

In the late 1940s the quadrilateral socket was introduced to the United States, and during the intervening years since its introduction the "quad socket" has been the standard design for fitting a prosthetic limb to the residual thigh of an above-knee amputee. During the more than 30 years in which the quad socket has been employed in the United States it has become clear, however, that there are certain problems, particularly as to comfort and stability, inherent to the use of the quad socket.

Although there are many variations to the quad socket, it consistently presents a horizontally oriented brim at the proximal posterior. The horizontal brim serves as the ischial seat upon which the user's ischial tuberosity is supported. In fact, that portion of the user's weight which would normally have been supported by the amputated limb is transferred to the quad socket through the ischial seat.

The geometry of the quad socket purposely provides a rather narrow dimension, measured between the anterior and posterior walls of the socket, in relation to the medial/lateral dimension. The aforesaid dimensional relationship of the quad socket was selected to assure that the socket applies pressure on the anterior of the residual thigh to push the ischium toward the posterior of the socket in order that the ischial tuberosity will be forced to rest solidly on the ischial seat presented by the brim at the proximal posterior of the socket. To accommodate the compression of the thigh which results within the quad socket because of the purposely narrowed anterior/posterior dimension, the medial/lateral dimension of the socket is made relatively larger.

However, the enlarged medial/lateral dimension makes it virtually impossible to provide sufficient lateral support for the distal end of the femur in the residual limb, as would be required to eliminate a limp during that portion of the user's gait when the artificial limb is in the weight bearing mode and the sound leg is swinging through to the next step. In fact, many knowledgeable commentators are of the opinion that the quad socket is ineffective in all but the mid-stance phase of the gait due to the excessive abduction of the femur permitted within the quad socket because of the aforesaid dimensional relationship.

Recognition of the deficiencies inherent to the quad socket is, in effect, a challenge to the basic concept that the ischial tuberosity should serve to transmit the majority of the weight expected to be carried by the residual limb to the ischial seat provided for that purpose on the quad socket. Such a challenge recognizes that the structural arrangement of the quad socket has the basic inability to stabilize the femur when the gluteus medius fires; the arrangement of the quad socket, after all, provides no structure whereby the ischium is able to preclude abduction of the femur. It is this inability to stabilize the femur which results in the necessity for the user to lean laterally in an attempt to stabilize the pelvis, thus presenting the readily recognizable, and characteristic, limp required of a person using the quad socket.

Specifically, as the gluteus medius pulls the femur into abduction, the pelvis slides medially because the ischial tuberosity is free to shift along the ischial seat of the quad socket; The unsupported femur has little choice but to abduct in a more pronounced attitude within the wide medial/lateral dimension of the quad socket. The pronounced abduction imposes pain at the distal end of the femur as well as at the proximal medial portion thereof. To reduce the undesirable pressure, and the resulting pain, the patient leans to position the torso over the abducted, distal end of the femur.

The aforesaid, negative characteristics of the quad socket tend to be obviated by a much more recent innovation in prosthetic sockets which employs a narrower medial/lateral dimension and a wider anterior/posterior dimension, the relative dimensions being chosen such that the ischial tuberosity and a portion of the ramus of the ischium is ostensibly to be contained within the socket. The recently developed, narrow medial/lateral socket configuration also employs a relatively high lateral wall which provides medially directed reactive forces proximal and distal to the greater trochanter. In this arrangement the abduction angle of the femur in the residual limb more closely approaches that of the femur in the sound extremity during all portions of the user's gait, thus greatly reducing the characteristic limp. This recently developed socket design is not, however, designed by a universally accepted appellation. At present such a socket design is designated as a "N.S.N.A (Normal Shape and Normal Alignment) socket", or a "narrow ML (Medial/Lateral) socket" or a "Cat-Cam (Contoured, Adducted Trochanter, Controlled Alignment Method) socket".

Irrespective of the name employed, although it is believed that the term "Ischial Containment Socket" is most appropriate, in order to provide an effective socket which incorporates the narrow medial/lateral dimension a more precise fitting of the socket to each patient has heretofore been required, as are multiple tests of the socket prior to fabrication of the finished prosthetic limb. Because of the difficulty in achieving a functionally acceptable fit with this new design, more fitting time is required, and the patient must be willing to accept this inconvenience. Nevertheless, the greater comfort and the improved functionality that can be achieved by this new design has been thought to offset the inconvenience, and increased cost, at least to those who can afford both the time and expense.

SUMMARY OF THE INVENTION

It is therefore, a primary object of the present invention to provide an improved prosthetic device in the nature of an ischial containment socket for securing an artificial limb to the residual thigh of an above-knee amputee, the improved socket incorporating the narrow, medial/lateral dimensional relationship.

It is a another object of the present invention to provide an ischial containment socket, as above, which employs an interface and a separate frame in order to facilitate adjusting the geometry of the socket—namely, the longitudinal dimension of the interface, the rotative disposition of the frame relative to the interface as well as the canting of the frame relative to the interface.

It is a further object of the present invention to provide an ischial containment socket, as above, wherein the peripheral dimensions of a relatively small number of standard interface sizes can be selectively adjusted to accommodate the majority of users without the extensive fitting and testing heretofore deemed necessary.

It is still another object of the present invention to provide an ischial containment socket, as above, which can be manufactured and fitted at considerably less expense than heretofore contemplated.

These and other objects of the invention, as well as the advantages thereof over existing and prior art forms, which will be apparent in view of the following detailed specification, are accomplished by means hereinafter described and claimed.

In general, an ischial containment socket—i.e., one having a relatively narrow, medial/lateral dimension—embodying the concepts of the present invention employs an interface having proximal and distal ends. At least the proximal end of the interface is open to receive a residual limb, and the proximal ends on the adjacent portions of the merged posterior and medial walls in the interface present a brim having a reversely curved containment recess.

Means are provided to achieve selective adjustment of the peripheral dimensions along the longitudinal extent of the interface so that it will be readily adapted properly to circumscribe residual limbs having a wide range of circumferential measurements. The preferred manner by which to effect the necessary selective adjustment is to make the interface peripherally discontinuous along the longitudinal extent thereof and to employ cinch means by which to secure the peripheral discontinuity in the desired relation whereby the interface properly circumscribes the residual limb received therein.

A frame is located at the distal end of the interface, and means are provided selectively to secure the frame to the interface in the desired relative disposition.

One exemplary ischial containment socket, and a modification thereof, both embodying the concepts of the present invention are shown by way of example in the accompanying drawings and are described in detail without attempting to show all of the various forms and modifications in which the invention might be embodied; the invention being measured by the appended claims and not by the details of the specification.

BRIEF DESCRIPTION OF THE DRAWINGS

FIG. 1 is a perspective view which primarily depicts the exterior surfaces of the lateral and anterior walls on an ischial containment socket embodying the concepts of the present invention and adapted for use in attaching a prosthetic limb to the left, residual thigh of an above-knee amputee;

FIG. 2 is also a perspective view, but one which primarily depicts the exterior surfaces of the anterior and medial walls in the ischial containment socket depicted in FIG. 1;

FIG. 3 is a side elevation, partly in section, taken from the medial side of the ischial containment socket depicted in FIGS. 1 and 2;

FIG. 4 is a transverse section taken substantially along line 4—4 of FIG. 3;

FIG. 5 is a bottom plan view taken substantially along line 5—5 of FIG. 3;

FIG. 6 is a moderately reduced, top plan view taken substantially along line 6—6 of FIG. 3;

FIG. 7 is an exploded perspective primarily depicting not only the medial and anterior surfaces of the interface employed in either the exemplary, or the modified, arrangement of the ischial containment socket disclosed herein but also the corresponding surfaces of a frame which is conjoined to the interface to form an ischial containment socket embodying the concepts of the present invention; and, FIG. 8 is a vertical section taken through a modification of an ischial containment socket such as depicted in the foregoing FIGS., said vertical section representing the interior surface on the anterior wall of said socket.

DESCRIPTION OF AN EXEMPLARY EMBODIMENT

An ischial containment socket embodying the concepts of the present invention is designated generally by the numeral 10 on the attached drawings.

The socket 10 employs an interface 11 to which a frame 12 can be selectively secured. Attached components 13 by which the knee joint (not shown) of a prosthetic limb can be secured in a well known manner are presented from the frame 12, and the attachment components 13 will hereinafter be more fully described.

The interface 11 has open proximal and distal ends 14 and 15, respectively. The interface 11 also tapers progressively from the proximal end 14 to the distal end 15 such that the peripheral dimension of the interface 11 is greater at the proximal end 14 than it is at the distal end 15.

The residual thigh of an above-knee amputee is received through the open, proximal end 14 of the interface 11, and in order to accommodate the residual limb in the desired manner, the interface 11 has a posterior wall 16 which merges into opposed medial and lateral walls 18 and 19, respectively.

The lateral wall 19, in turn, merges into an anterior wall 20. The medial wall 18 merges into, and terminates, as an extension 22 which is disposed parallel to the anterior wall 20. In fact, the extension 22 and the anterior wall 20 are disposed in overlapping relation to form a lap joint 25.

The overlapping relation of the extension 22 and the anterior wall 20 thereby also effects a peripheral discontinuity 26 which extends the full longitudinal length of the interface 11. That is, the discontinuity 26 extends between the proximal and distal ends 14 and 15 of the interface 11.

The discontinuity 26 permits the peripheral dimension of the interface 11 to be adjusted by sliding the contiguously juxtaposed, and overlapping, extension 22 and anterior wall 20 in whatever direction is required to vary the extent to which they overlap. The extent of the overlap can also be progressively varied, to some degree, between the proximal and distal ends 14 and 15 in order to accommodate the particular "conicity" of the residual thigh received therein.

A plurality of cinches 28 may be employed to secure the lap joint 25 and thus the degree to which the extension 22 is required to overlap the anterior wall 20 in order to effect the desired conformity of the interface 11 with the residual limb. An exemplary configuration for the cinches 25 will be hereinafter more fully described.

The spacing—i.e., the dimensional separation—of the four walls 16, 18, 19 and 20 which define the interface 11 is preferably selected so that the dimension between the posterior and anterior walls 16 and 20 is greater than the dimension between the medial and lateral walls 18 and 19, respectively. This dimensional relationship is most clearly depicted in FIG. 6. The same dimensional relationship is also represented in FIGS. 2 and 7, but because of the foreshortening inherent to perspective views—which is visually exaggerated when the vertical extent of the medial wall 18 (which lies closer to the viewer) is markedly less than the vertical extent of the remotely located, lateral wall 19, as is the situation in FIGS. 2 and 7—one might tend to obtain the impression that the dimensional relationship of the spacial separation between the medial/lateral and the anterior/posterior walls of a socket 10 embodying the concepts of the present invention is similar to that of the quad socket, when, in fact, it is quite antipodal.

Continuing with the description of the structural details, the proximal end portions of both the posterior wall 16 and the medial wall 18, at least in proximity to the juncture of those walls, terminate in a containment brim 30. That is, a flared offset wall 31 extends generally outwardly and upwardly from the proximal ends of the adjacent posterior and medial walls 16 and 18, respectively. A reversely curved containment recess 32 is provided in the flared offset wall 31 at least in that portion of the brim 30 adjacent the merged posterior and medial walls 16 and 18. As such, the brim 30 presents a posterior-medial, reversely curved, containment recess 32. The containment recess 32 is thus disposed to assure that the ischial tuberosity 33 and the associated ramus 34 (FIG. 8) of the ischium are contained within the open, proximal end 14 of the interface 11.

The proximal end of the lateral wall 19 presents a reaction flange 35 which extends proximally relative to the greater trochanter 36 of the femur 38 when a patient's limb is positioned within the interface 11. The use of the reaction flange 35 in combination with the narrow medial/lateral dimension (relative to the anterior/posterior dimension of the interface 11) and the reversely curved containment recess 32 in the flared offset wall 31 of the containment brim 30 effectively contains the ischial tuberosity 33 and associated ramus 34 of the ischium within the confines of the interface 11.

Prior art sockets, even those which use many of the newly developed dimensional relationships that afford the narrow medial/lateral dimension, allow the ischial tuberosity to slip out of the socket proper and migrate medially along the proximal brim. When this occurs, the femur abducts and the superior lateral portion of the prosthetic socket drifts laterally under the patient. In short, the ischial tuberosity is not actually contained by prior art socket configurations, but the structural arrangement of the interface 11 embodying the concepts of the present invention does not achieve containment. In addition, the reaction flange 35 on the lateral wall 19 of the improved socket 10 snugly presses against the intraillio-trochanteric region to reduce the need for external support even further.

The interface 11 must be sufficiently rigid to provide the necessary columnar strength required to support the various compressive and bending loads applied thereto and yet be made of a material that can be trimmed to accommodate adjustment as well as providing a degree of flexion in order to absorb shock loading when the patient is walking. One suitable material from which to make the interface 11 would be a thermoplastic such as a low density polyethylene.

The frame 12 is preferably fabricated to be considerably more rigid than the interface 11, and as such the frame 12 can be conveniently fabricated from one of the many fiber reinforced plastics well known to the art or from a thermoplastic polyolefin such as polypropylene. Such a frame 12 has a cup-like portion 40 to receive the distal end 15 of the interface 11. The cup-like portion 40 has a generally planar base 41 that is circumscribed by a peripheral flange 42. Diametrically opposed mounting tangs 43A and 43B extend upwardly from the peripheral flange 42 to be selectively secured to the interface 11. For example, the tangs 43A and 43B, which preferably extend longitudinally along approximately the complete lower half of the interface 11, may be permanently riveted to the appropriate walls of the interface 11. However, to facilitate the abbreviated customization afforded by the ischial containment socket 10 embodying the concepts of the present invention, it has been found desirable demountably to attach the tangs 43A and 43B to the interface 11 by the use of threaded rivets 44 which are commonly known as "two piece screws" or "Chicago screws." A threaded rivet 44 may also be employed to secure the peripheral flange 43 of the frame 12 to at least the posterior wall 16 of the interface 11.

As may best be seen from FIG. 8, the threaded rivets 44 comprise an internally threaded ferrule 45 which extends perpendicularly outwardly from a low profile, smooth-surfaced, head 46 that can be disposed against the interior surface 48 of the interface 11 when the ferrule 45 is received within a bore 49 through the interface 11. A round headed machine screw 50 may be threaded into the ferrule 45 from exteriorly of the interface 11 and tightened through bore 51 in the tangs 43 that register with the bores 49 in the interface 11 to secure the tangs 43 against the exterior surface 52 of the interface 11. As depicted in the drawings, tang 43A may be secured to the lateral wall 19, and tang 43B may be secured to the medial wall 18.

The threaded rivets 44 may also be employed to secure the straps 55 and the turning buckles 56 of the cinches 28 to the exterior surface 52 of the interface 11. As represented in FIG. 1, one end of each strap 55A and 55B is fixedly secured to the interface 11 by the threaded rivets 44 which secure the tang 43A to the lateral wall 19. Corresponding turning buckles 56A and 56B are mounted to the interface 11 by virtue of the threaded rivets 44 which secure the tang 43B to the medial wall 18. One end of a third strap 55C may be fixedly secured to the lateral wall 19, as by a standard rivet 58, and a third turning buckle 56C may be secured to the medial wall 18, also by standard, but separate, rivet 58.

The free ends of the straps 55 are received through the appropriate turning buckles 56 and may be secured back upon themselves by the use of a Velcro fastening material 59 appropriately attached to the straps 55, as depicted.

The plurality of straps 55 may be effectively employed selectively to adjust, and secure, the lap joint 25 so as to provide the required peripheral dimension of the interface 11 along its longitudinal extent such that the interface 11 will properly circumscribe the residual limb received therein. The capability of selecting the peripheral dimensions of the interface 11 along the longitudinal extent thereof is one aspect of the adjustability achieved by virtue of the concepts of the present invention. This peripheral adjustability makes it feasible, for example, to provide the interface 11 in three sizes—small, medium and large —and effect the necessary fine adjustment necessary to fit the residual limb of a particular individual by selectively varying the extent to which the extension 22 overlaps the anterior wall 20 and securing the desired overlap with the cinches 25.

By making the interface 11 of a material, such as low density polyethylene, which can be fairly easily trimmed, one can readily provide the desired longitudinal dimension to the interface. In addition, providing a means selectively to secure the frame 12 to the interface 11 also affords the prosthetist with the capability rather easily to provide the desired angular disposition of the frame 12 with respect to the interface 11. That is, the prosthetist can not only rotate the frame 12 relative to the longitudinal axis of the interface, but can also cant the frame 12 relative to the interface 11 to provide the desired disposition of one element with respect to the other before locating and drilling the bores 49 in register with the bores 51 in the tangs 43. Thus, when the frame 12 is secured to the interface 11, the resulting socket 10 has been properly, easily and inexpensively customized as to the dimensions and dispositions heretofore discussed in order further to establish the geometry of the socket 10 so that it can fit virtually any user without the extensive fitting and testing heretofore deemed necessary.

For comfort, a cushion 60, such as a piece of sponge rubber or the like, may be disposed on the planar base 41 of the frame 12, as depicted in FIG. 3, to be accessible for contact by the distal end of the residual limb received within the socket 10.

The attachment components 13, which may be four, spaced, flat-head bolts, are presented from, and extend through, the planar base 41 of the frame 12. A ring washer 61, or even a plurality of individual washers, may be employed to distribute the forces applied by the attachment components 13 across a relatively large area of the planar base 41 of the frame 12. In any event, the cushion 60 is disposed above the attachment components 13 and the washer(s) 61 exposed within the socket 10.

In the modified socket 110 depicted in FIG. 8 the length of the bolts comprising the attachment components 113 may be selected, in conjunction with spacers 62 such as the tubular elements depicted, to locate a pedestal plate 63 at the desired location upwardly from the base 41 of the frame 12 so that the cushion 60 may be received thereon and be at the proper height for a particular patient. Inasmuch as the use of a pedestal plate 63 and associated spacers 62 in combination with elongated attachment components 113 are the only differences between the modified ischial containment socket 110 and the exemplary socket 10, all other reference numbers on the modified socket 110 depicted in FIG. 8 are the same as the reference numbers employed with the exemplary socket 10 depicted in FIGS. 1-7, inclusive.

It should, therefore, now be apparent that a prosthetic socket embodying the concepts of the present invention fully accomplishes the objects thereof.

I claim:
1. A prosthetic socket for above-knee amputations comprising:
   an interface having proximal and distal ends, said proximal and distal ends both being open;
   a single peripheral discontinuity;
   said peripheral discontinuity extending along the entire longitudinal extent of said interface between said proximal and distal ends to permit adjustment of the peripheral dimension of said interface along the full longitudinal extent thereof;
   means selectively to secure the selectively adjusted peripheral dimension of said interface so that it will properly circumscribe a residual limb received within said interface;
   a frame positioned at the distal end of said interface; wherein
   said frame incorporates a cup-like portion to receive the distal end of said interface;
   mounting tangs extend upwardly from said cup-like portion; and
   said means selectively to secure said frame to the distal end of said interface are connected through said tangs.

2. A prosthetic socket, as set forth in claim 1, wherein:
   said cup-like portion has a planar base;
   said tangs are supported by, and extend upwardly of, said planar base; and,
   cushion means are supported proximally of said planar base interiorly of said interface.

3. A prosthetic socket, as set forth in claim 2, wherein:
   pedestal means extend upwardly from said planar base; and
   said cushion is supported on said pedestal means.

4. A prosthetic socket, as set forth in claim 3, wherein:
   means are provided to select the height of said pedestal means upwardly of said planar base.

5. A prosthetic socket, as set forth in claim 1, wherein:
   said interface has medial and lateral walls; and,
   said mounting tangs are disposed along the medial and lateral walls of said interface.

6. A prosthetic socket, as set forth in claim 5, wherein:
   said mounting tangs are disposed exteriorly of said interface.

7. A prosthetic socket, as set forth in claim 6 wherein:
   a reaction flange is presented from the proximal end of said lateral wall, said reaction flange being inwardly curved to press snugly against the intrailliotrochanteric region of the residual limb.

8. A prosthetic socket, as set forth in claim 6, wherein:
   said interface is peripherally discontinuous along the longitudinal extent thereof which extends between said proximal and distal ends, the longitudinal extent of said discontinuity presenting opposed, overlapping portions to accommodate adjustment of the peripheral dimension of said interface.

9. A prosthetic socket, as set forth in claim 8, wherein:
   said interface also has anterior and posterior walls, the dimension between said anterior and posterior walls being greater than the dimension between said medial and lateral walls.

* * * * *